United States Patent
Edblad

(10) Patent No.: US 8,262,913 B2
(45) Date of Patent: Sep. 11, 2012

(54) COLUMN PACKING METHOD

(75) Inventor: Niklas Edblad, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 13/303,290

(22) Filed: Nov. 23, 2011

(65) Prior Publication Data

US 2012/0073698 A1   Mar. 29, 2012

Related U.S. Application Data

(62) Division of application No. 12/994,174, filed as application No. PCT/SE2009/050601 on May 26, 2009, now Pat. No. 8,066,882.

(30) Foreign Application Priority Data

May 30, 2008   (SE) ...................................... 0801283

(51) Int. Cl.
*B01D 15/08*   (2006.01)
(52) U.S. Cl. ...................... 210/656; 210/143; 210/198.2
(58) Field of Classification Search .................. 210/635, 210/656, 143, 198.2, 232; 141/12, 73, 80
See application file for complete search history.

(56) References Cited

U.S. PATENT DOCUMENTS

| | | | |
|---|---|---|---|
| 7,452,471 B2 * | 11/2008 | Windahl | 210/656 |
| 2007/0012626 A1 | 1/2007 | Andersson et al. | |
| 2007/0090053 A1 * | 4/2007 | Windahl | 210/656 |
| 2011/0077766 A1 * | 3/2011 | Karlsson et al. | 700/110 |

FOREIGN PATENT DOCUMENTS

| | | |
|---|---|---|
| WO | WO 2007/045491 | 4/2007 |
| WO | WO 2009/093953 | 7/2009 |

OTHER PUBLICATIONS

Levison, P., et al., Journal of Chromatography A, (1999), 865(1-2):3-12.
EP Supplemental Search Report on Copending Application 09755153.5 Dated May 23, 2012.

* cited by examiner

*Primary Examiner* — Ernest G Therkorn

(57) ABSTRACT

A method for packing a media bed in a column (3) from a slurry being a dispersion of said media particles and a liquid, said method comprising the steps of: a) estimating a slurry concentration; b) filling the column (3) with a certain volume of the slurry from a slurry tank (13) connected to the column; c) packing a test media bed from the slurry; d) detecting where the test media bed is consolidated; e) use the information about the consolidated test media bed height for providing to the column an amount of slurry that after further packing will give a user target bed height; f) packing a media bed from the slurry.

3 Claims, 2 Drawing Sheets

COLUMN PACKING METHOD

CROSS-REFERENCE TO RELATED APPLICATIONS

This application is a divisional of U.S. patent application Ser. No. 12/994,174 filed Nov. 23, 2010, now U.S. Pat. No. 8,066,882, which is a filing under 35 U.S.C. §371 and claims priority to international patent application number PCT/SE2009/050601 filed May 26, 2009, published on Dec. 3, 2009 as WO 2009/145715, which claims priority to application number 0801283-3 filed in Sweden on May 30, 2008.

FIELD OF THE INVENTION

The present invention relates to a media packing system for columns and media packing methods for use in columns. More specifically, the invention relates to methods for improving the quality, ease and consistency of packing chromatography media into chromatography columns.

BACKGROUND OF THE INVENTION

Columns used in liquid chromatography typically comprise a tubular body enclosing a packed bed of porous chromatography medium through which a carrier liquid flows, with separation taking place by material collection between the carrier liquid and solid phase of the porous medium. Typically, the medium is enclosed in the column as a packed bed formed by consolidating a suspension of discrete particles, known as slurry that is pumped, poured, or sucked into the column. Consolidation of the slurry into a consolidated packed bed is achieved by compressing the slurry so that it is packed into a volume, which is less than the volume that it would have occupied if it had been allowed to settle under the influence of gravity to form a sedimented bed. The efficiency of subsequent chromatographic separation relies strongly on 1) the liquid distribution and collection system at the fluid inlet and outlet of the packed bed, 2) on the spatial orientation (also know as the packing geometry) of the media particles in the packed bed, and 3) on the compression of the packed bed. If the compression of the packed bed is too low then chromatographic separations performed on that bed suffer from "tailing" and, generally, such insufficiently compressed beds are unstable. If the compression of the packed bed is too high then chromatographic separations performed by the bed suffer from "leading" and such over-compressed beds can affect throughput and binding capacity, and, in general, give much higher operating pressures. If the compression is optimum, then the separation peaks formed during use exhibit much less leading or tailing and are substantially symmetrical. The optimum degree of compression required for a column is determined experimentally for each column size (width or diameter), bed height, and media type.

Prior to any separation process, the bed has to be prepared by starting from the slurry of particles that has to be introduced into the column. The process of bed formation is called 'the packing procedure' and a correctly packed bed is a critical factor influencing the performance of a packed bed. One of the primary goals of the packing procedure is to provide a bed, which is compressed by the optimum amount of compression, i.e. the optimum compression factor. The height of the bed which often is user defined when it is optimally compressed is called the target compressed bed height.

Large-scale columns can be prepared by suctioning or injecting into the column a predetermined volume of slurry having a specified concentration of media particles. Once the predetermined volume of slurry has been delivered into the column it needs to be consolidated and compressed. This can be accomplished for example by moving a movable adapter down the longitudinal axis of the column towards the bottom of the column, normally at a constant speed push both liquid and particles towards the bottom of the column. The excess liquid during this procedure is expelled at the column outlet, while the media particles are retained by means of a filter material, a so-called 'bed support', with pores too small to allow the media particles to pass through. The packing process is complete once the packed bed has been compressed by the optimum degree of compression. There are alternative ways of packing that can be used in this invention. For example a flow can be applied to force the particles in the slurry to move towards the outlet of the column instead of moving an adapter downwards. A further alternative is to use spray nozzles spraying in slurry until a packed bed is achieved. These methods will be further described below. The packing process is considered successful if the compressed bed allows for a good and robust chromatographic performance. However, packing such an optimally compressed bed of chromatography media in a chromatography column by manual means is not easy to accomplish in practice due to the fact that the quality of the final packed bed depends to a great extent on the skill of the operator. During filling and subsequent packing of the column, the operator manually selects and adjusts all packing parameters such as valve positions, pump speed, adapter's speed of movement, etc. The operator has to measure the slurry concentration in order to decide how much slurry that should be filled into the column. If the measure of the slurry concentration is not exact (which is often the case because it is hard to measure the slurry concentration exactly) the volume of the slurry filled into the column is not optimal and the consolidated bed will settle at a bed height that was not expected (as calculated from the measured slurry concentration) and hereby the target packing factor can not be achieved at target bed height. Furthermore, the operator also has to judge the point when the adapter starts compressing the bed. This point is used to calculate how much further the adapter must move in order to obtain the required amount of compression. Mistakes in the selection of any of the packing parameters normally lead to an under performing column. Further, in columns equipped with a transparent tube it may be difficult, and in columns equipped with a non-transparent tube such as stainless steel it is impossible, to judge by eye when compression of the bed actually starts and a significant error at this point makes it impossible to obtain an optimally compressed bed.

There is also a risk of damaging the media and the column if the user takes wrong decisions.

Therefore, there is a need for a system and method for the accurate and reproducible packing of chromatography media into chromatography columns.

SUMMARY OF THE INVENTION

An object of the invention is to provide a column packing system and a method for packing media into columns in order to overcome the drawbacks of the prior art systems.

This is achieved in a method, in a computer program product and in a control unit.

Hereby a test bed is first packed and the height of this test bed is measured and used in order to be able to calculate how much slurry that should be provided to the column to achieve a final user target bed height. This finally packed bed will be very close to predefined wanted conditions of the bed because the measure of the slurry concentration was very good when calculated from the test bed height.

In one embodiment the test bed is unpacked and diluted to a known slurry concentration. Then the column is filled with a volume of the slurry calculated from a user target bed height and this new known slurry concentration. The test bed could either be a small test bed that will be packed rather fast end is easy to unpack. In this case the unpacked test bed is suitably taken back to the slurry tank and diluted back to the same slurry concentration as any remaining slurry in the slurry tank. Alternatively all the slurry in the slurry tank can be used for the test bed. This can be suitable since in this case the media need not be diluted back to exactly the same slurry concentration as from the beginning but can be diluted to any suitable slurry concentration. This is because the slurry tank is empty when the unpacked bed is taken back there.

In another embodiment the test bed is small and it is kept inside the column when more slurry is added. The slurry concentration of the slurry remaining in the slurry tank is calculated based on the consolidated test bed height and the volume of slurry initially filled into the column. This slurry concentration and the user target bed height is used for calculating how much more slurry that is needed to be filled into the column such that the test bed and the new slurry together will form a bed with the user target bed height.

Further embodiments of the invention are described in the dependent claims.

DETAILED DESCRIPTION OF THE INVENTION

The presently preferred embodiments of the invention are described with reference to the drawings. The descriptions of the preferred embodiments are exemplary and are not intended to limit the scope of the invention.

As used herein and in the appended claims:

The term "column" is intended to include the terms "vessel" and "cell", as well as any other structure utilized by practitioners of the separation arts, to effect a separation, and/or reaction, and/or catalyzation, and/or extraction of components from an admixture by bringing the admixture into contact with solid or liquid exchange media, known as the packed bed.

The term "slurry" is a dispersion of media particles and liquid.

The term "longitudinal direction of flow" refers to the direction of flow from an inlet towards an outlet within a column. "Longitudinal" is used consistently to designate the dominant flow path of fluid through a cell without regard to direction.

The term "distribution system" refers to structures through which fluids are introduced to a column and the term "collection system" refers to structures used to collect fluids from a column.

The term "sedimented bed height" refers to the height of a bed of media particles which is obtained when a bed is formed after the media particles in a slurry are allowed to sediment under the influence of gravity only—such a bed is called a "sedimented bed".

The term "consolidated bed height" refers to the height of a bed of media particles that is obtained when a bed is formed in a column while the media particles in a slurry are forced to sediment when a flow of fluid is applied through the column in the longitudinal direction of flow either by 1) pumping liquid into the column, 2) by pumping liquid out of the column, or 3) by the movement (for example, the descent) of a movable adapter, which forces liquid out of the column—such a bed is called a "consolidated bed".

The term "compressed bed height" refers to the height of a bed of media particles in a column that is obtained when a consolidated or sedimented bed has been compressed, for example by contact with, and further movement of, a movable adapter or the like, or by pumping fluid through the column at a higher rate than that used during consolidation of the bed—such a bed is called a "compressed bed".

The term "compression factor" is defined as (the sedimented bed height)/(the compressed bed height) and the term "packing factor" is defined as (the consolidated bed height)/(the compressed bed height). Hereafter, when packing factor is used it should be understood that the compression factor could be used instead.

Figure 1:
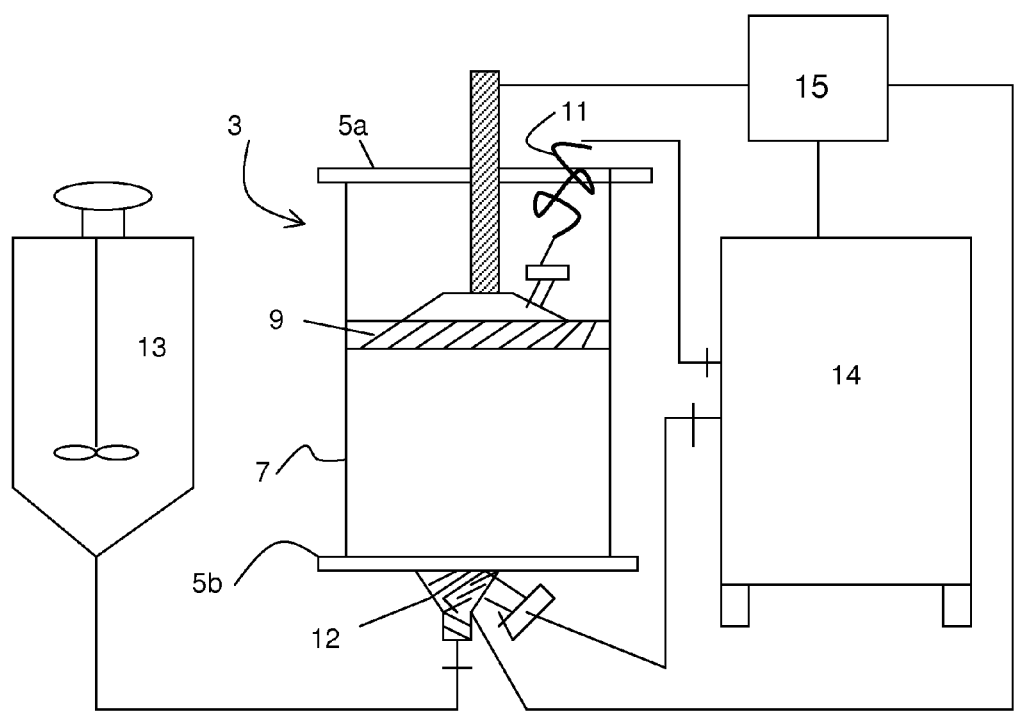
FIG. 1 is a schematic diagram of a media packing system according to one embodiment of the invention.

FIG. 1 is a schematic view of a column packing system according to one embodiment of the invention. The system comprises a column 3 which comprises upper lid or flange 5a and lower end plate 5b surrounded by a cylindrical column wall 7. Positioned between the lid or flange 5a and lower end plate 5b in the column 3 is a movable adapter 9 (which may be provided with a liquid distribution system, not shown, intended to distribute incoming liquid substantially evenly over the cross-section of the column 3, and a bed support, not shown, extending over the cross-section of the column with a mesh fine enough to prevent bed particles from passing through it) connected to a column inlet 11 connectable to a liquid delivering system 14 which delivers liquids such as sample mixtures, eluants, buffers etc. Movable adapter 9 is movable in the longitudinal direction of the column by an actuator (not shown), such as an electric, hydraulic or pneumatic motor or piston/cylinder actuator.

Slurry can be sucked into the column 3 through a nozzle or valve 12 positioned in the bottom of the column. The nozzle or valve 12 is connected to a slurry tank 13. Movable adapter 9 is provided with a positioning means (not shown) to determine the position ("x") of the movable adapter relative to a fixed level, for example the upper side of the lower end plate 5b, and a signal corresponding to the distance x is sent to a control unit 15 which in this example is connected to the liquid delivering system 14, to the adapter actuator and to the nozzle or valve 12 that is connected to the slurry tank. The control unit 15 could however instead be built into the liquid delivering system 14. The operation of the actuator and the corresponding up or downwards movement of the movable adapter 9 is controllable by the control unit 15. Control unit 15 preferably comprises hardware and software for controlling the operation of the column 3. The control unit 15 controls for example the opening and closing of valves and the speed of the movable adapter movement.

In FIG. 1 one example of a column is shown. However there are other types of columns where the packing process according to the invention also can be used. For example the packing does not necessarily need to be performed by moving an adapter downwards. Another example of a packing process is a column where the adapter is placed at the intended final packed bed height and the column is filled and packed at the same time through the nozzle in the top of the column. As slurry is being sprayed into the column, excess liquid will leave the column through the bottom bed support. The particles of the slurry will be retained by the bed support and a bed will build up from the bottom. When the correct amount of slurry has been delivered from the slurry tank to the column, the packing pump can be shut off and the nozzle retracted. To unpack the column, use the spray action to break up the bed. Eventually the bed is broken up and the slurry can be pumped out through the column.

Another possible solution is to combine this packing method with a moveable adapter. The column can be packed as described above but this time the bed is not compressed. Instead the adapter is used for the final compression.

The column described in FIG. 1 is also possible to pack in another way than described above. Instead of creating the liquid flow through the downwards movement of the adapter, it can remain in the filling position while a liquid flow through the top bed support is used to consolidate or pack the bed. The flow rate can be varied so that the bed is first consolidated and then packed. At the end, when the bed is compressed through flow the adapter can be lowered to the bed surface to prevent it from expanding.

Figure 2:
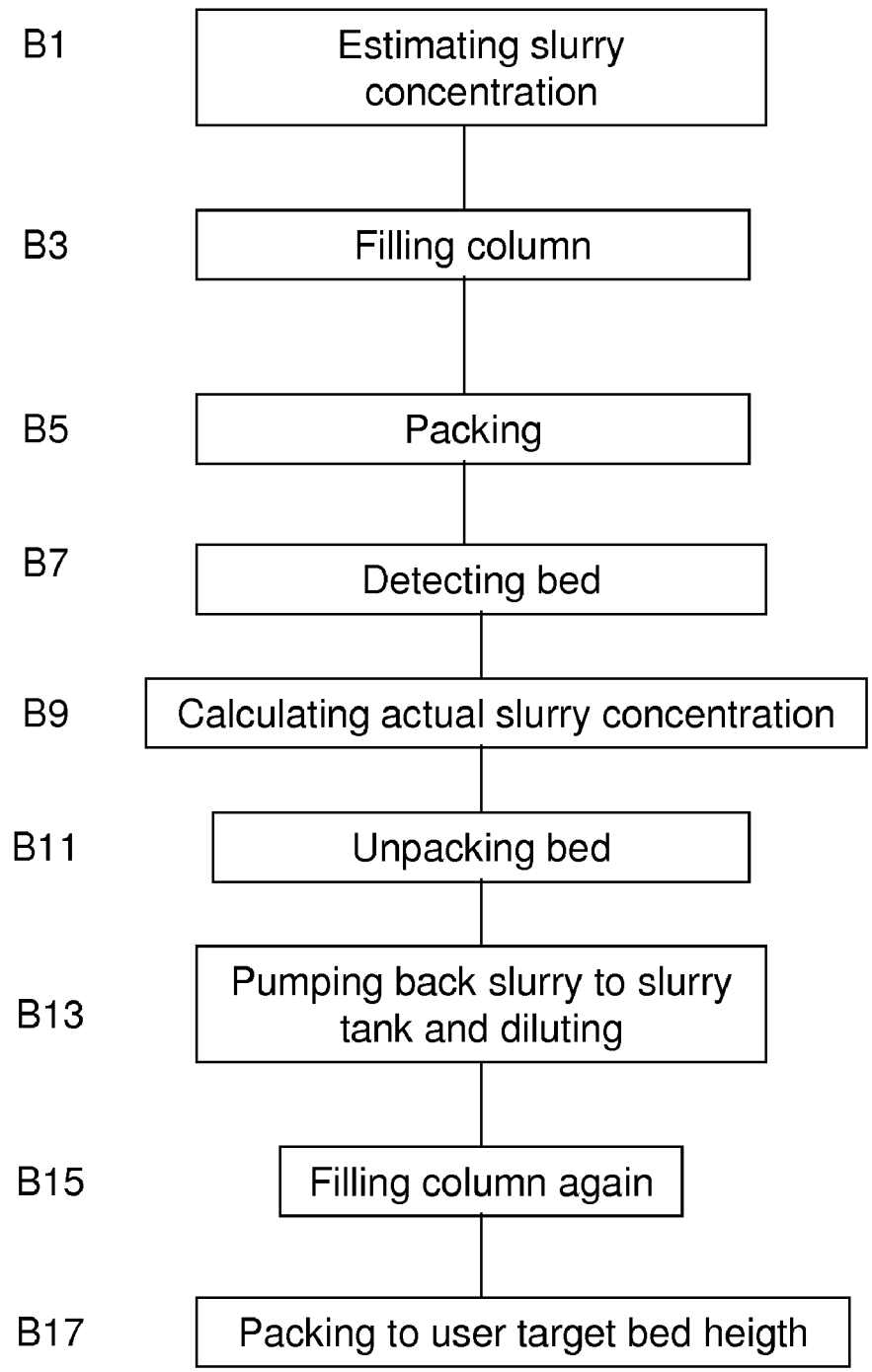
FIG. 2 is a flow chart describing the packing method according to one embodiment of the invention.

According to this invention a process for packing a column is provided. FIG. 2 is a flow chart of the process of packing a column according to one embodiment of the invention. The steps are described in order below:

B1: A slurry concentration of the slurry inside the slurry tank (13) is estimated. This only needs to be a roughly estimated concentration. In practice the user either enters a value of the estimated slurry concentration into the control unit or chooses from a predefined list of values of slurry concentrations. Alternatively the same default value for estimated slurry concentration can always be used. In this case this value is pre-programmed into the control unit.

B3: The column is filled with a certain amount of slurry. To calculate this amount of slurry the estimated slurry concentration is used and a target test bed height. The target test bed height can in one embodiment of the invention suitably be comparatively small in order to speed up this first part of the method where a test bed is packed in order to measure the slurry concentration. However in another embodiment all the slurry in the slurry tank can be used in this step. This will be further described below.

B5: The packing is started, i.e. in the example where a movable adapter is used for the packing the adapter is lowered inside the column and liquid is pressed out through the lower end plate 5b of the column as the media bed is formed inside the column.

B7: The bed is detected, i.e. the media bed has been formed and this can be detected by for example the known pressure dip technique. With this technique the pressure is measured in the column and when the media bed is formed the pressure will change and this can be detected. Alternatively the motor current of the adaptor can be watched. The motor current will raise when bed is detected.

B9: The actual slurry concentration (of the slurry initially filled into the column and any slurry remaining in the slurry tank) can now be calculated by using the detected bed height and the slurry volume initially filled into the column. In the embodiment where all slurry is used for the test bed the initial slurry concentration need not be calculated but any new wanted slurry concentration can be achieved during unpacking (this will be further described below).

B11: The bed is unpacked. (In another embodiment the test bed is preferably small and need not to be unpacked but can remain inside the column when more slurry is filled in—this will be described below) The column can be unpacked in many ways, by the combined effects of the pump system delivering liquid flow in through either of the mobile phases, the upwards or downwards movement of the adapter and by utilizing valves through which liquid can be pumped in and out of the column. The whole process can be monitored and controlled by measuring critical parameters such as column pressure, adapter position and flow rate. If the column is equipped with means for spraying liquid or slurry into the column, these pumps can be automated as well. In this case the bed structure is broken by the spray action and the resulting slurry can be pumped out of the column. The bed can be expanded by running the adapter upwards at the same time as liquid is delivered through the bottom mobile phase. This will lift the bed from the bottom screens and allow it to expand to and/or past the point of the uncompressed bed. Pushing the bed up with a liquid layer underneath will make the bed to break apart and fall to the bottom. A push of liquid from the top column inlet can help to speed up the break-up of the bed. At this point, the bottom valve is opened and a slow liquid flow through the bottom screen is started to keep media from being packed against the bottom screen again. The adapter is run downwards and thereby forcing the slurry to exit through the bottom media valve. Both the adapter speed and the liquid speed through the bottom screen can vary throughout the process to yield the best unpacking conditions and to reach a certain end slurry concentration. The adapter is run all the way down to its bottom position and the remaining media can be flushed out. The column is now ready for another cycle. Another option to unpack the column is to pull and push slurry back and forth from and to the column to break up the bed. Yet another option is to close all column inlets and create an under-pressure in the column which pulls the bed apart. Suitably all liquids coming out from the column and being pumped into the column can be measured in this system. This is needed in order to be able to calculate the slurry concentration.

The benefit of this invention is that an almost exact measure of the slurry concentration can be achieved after this unpacking of the first packed test bed. This is possible because the amount of media is known from the test bed height. And this media can be diluted to a known slurry concentration. If there is more slurry in the slurry tank (as we assume for this first embodiment) we need to dilute the media back to the same slurry concentration when pumped back to the slurry tank. If liquid is added during the unpacking procedure this amount of liquid need to be measured.

B13: The media/slurry is pumped back into the slurry tank and the media/slurry is diluted back to the actual slurry concentration. This is done according to some of the discussions under B11 above. The system needs to remember the amounts of any liquid/slurry being pumped into or out from the column during unpacking.

B15: The column is filled with slurry a second time. This time the actual slurry concentration (which is a very good measure of the concentration) and the user target bed height is used to calculate the filling volume.

B17: The media bed is packed a second time. This time the adapter can run blindly down to the target bed height. The bed need not to be detected first. However it is also possible to use conventional packing methods with manual interaction steps if this is preferred. However the finally packed bed will be of better quality since the value used for slurry concentration is more accurate.

According to a second embodiment of the invention all slurry in the slurry tank is used for the packing of the test bed. Hereby the slurry that is taken back to the slurry tank when the test bed has been unpacked need not to be diluted to the same concentration as it had originally. Any suitable concentration is possible as long as the volume of all liquids in to and out from the column is remembered such that the measure of the slurry concentration is as good as possible. In this embodiment an air sensor is suitably provided between the slurry tank and the column in order to ensure that no air is sucked into the column when the slurry tank has been emptied.

According to a third embodiment of the invention the test bed is unpacked and forwarded to another tank than the original slurry tank. Also in this case the slurry needs not to be diluted to the exact same slurry concentration as it had originally. It is only important to remember all flows in and out in order to calculate the slurry concentration. In the second and third embodiments of the invention it is important that the test bed is at least the same height as the finally wanted bed. This is to ensure that there is enough slurry available during the second packing step.

According to a fourth embodiment of the invention the test bed is preferably small and can be kept inside the column when more slurry is filled in to the column. The slurry concentration of the slurry in the slurry tank can be calculated from the test bed height and initially filled volume of slurry. This will be a good measure of the slurry concentration according to the above discussion. Then it can be calculated how much more slurry that is needed to be provided to the column for forming the final bed. If the test bed was small it will be possible to force more slurry through the test bed (or alternatively more slurry can be provided to the column from the top of the column or through nozzles from other places of the column than the bottom.

According to a second aspect of the invention this packing process can be automated. A control unit that is either connected to the system or incorporated into the liquid delivering system, can comprise hard ware and soft ware in order to control the system such that at least some of the steps B1-B17 are performed automatically. The control unit can hereby control valves in order to fill the column with slurry, it controls the movement of the adapter, it receives signals from a pressure sensor such that it knows where the settled bed was detected and it can calculate the actual slurry concentration. Furthermore it can suitably automatically start the unpacking and control pumps in order to pump back media/slurry to the slurry tank. The control unit can furthermore preferably measure the exact amount of liquid coming out from the column during packing and being pumped into the column during unpacking and liquid being pumped into the slurry tank in order to dilute the slurry to a wanted slurry concentration. Finally the control unit can calculate a new filling volume and control the filling of the column a second time and control a new packing procedure. This is a very safe process and no manual interaction will be needed.

Hereby the control unit 15 comprises according to this aspect of the invention software such that the start and stop of these steps (some of them optionally) can be controlled automatically without any manual interactions. An operator preferably provides input data to the control unit 15 or chooses data from a pre-programmed list before the packing process is started. This data should include the estimated slurry concentration. It could also be other information regarding the actual packing to be performed such as for example media type, target bed height, column diameter and packing factor. Hereby the whole packing process can be fully automated.

The control unit 15 can also comprise software for guiding the user through the packing procedure. It can comprise a graphical user interface in which the user can follow the packing procedure and possibly also interrupt the procedure and control one or more parts of the process manually.

In one embodiment of the invention safety features such as means for monitoring for example over-pressurizing of the column or over-compressing of the medium can be included to ensure safe and fail proof operation. These monitoring means could be for example pressure gauges in liquid connection with the inside of the column, flow meters to control flow, air sensors to reduce the risk of applying air into the column, but also means to detect the amount of force that is applied onto the bed.

Although, the invention has been illustrated by examples of embodiments in which the column is cylindrical and has a constant diameter, which enables a linear correlation between cylinder volume and bed height, it is also conceivable to adapt the present invention for application to other column shapes in which the correlation is non-linear.

Even though the present invention has been described above in terms of specific embodiments, many modification and variations of this invention can be made as will be obvious to those skilled in the art, without departing from its spirit and scope as set forth in the following claims.

What is claimed is:

1. A method for packing a media bed in a column (3) from a slurry being a dispersion of said media particles and a liquid, said method comprising the steps of:
   a) estimating a slurry concentration;
   b) filling the column (3) with a certain volume of the slurry from a slurry tank (13) connected to the column;
   c) packing a test media bed from the slurry;
   d) detecting where the test media bed is consolidated;
   e) calculating a slurry concentration of slurry remaining in the slurry tank by using information from the consolidated test bed height and introducing more slurry of this known slurry concentration while the test bed is kept in the column, the amount of introduced slurry being controlled such that a user target bed height will be achieved after further packing; and
   f) packing a media bed from the slurry.

2. The method of claim 1, wherein the volume of slurry filled into the column under step b) is a comparatively small volume giving a comparatively small test bed under step d).

3. The method of claim 1, wherein at least some of the steps are controlled automatically from a control unit (15) connected to the system.

* * * * *